(12) United States Patent
Reitan et al.

(10) Patent No.: US 7,288,113 B2
(45) Date of Patent: Oct. 30, 2007

(54) TITANIUM INCUDO-STAPEDIAL JOINT PROSTHESIS

(75) Inventors: Harlan J. Reitan, Collierville, TN (US); Michael D. White, Olive Branch, MS (US); Anthony D. Prescott, Arlington, TN (US)

(73) Assignee: Clarity Corporation, Memphis, TN (US)

( * ) Notice: Subject to any disclaimer, the term of this patent is extended or adjusted under 35 U.S.C. 154(b) by 10 days.

(21) Appl. No.: 10/976,638

(22) Filed: Oct. 29, 2004

(65) Prior Publication Data

US 2006/0095129 A1  May 4, 2006

(51) Int. Cl.
*A61F 2/18* (2006.01)
(52) U.S. Cl. ...................................... 623/10
(58) Field of Classification Search .................. 623/10, 623/11.11, 13.18; 606/151–155
See application file for complete search history.

(56) References Cited

U.S. PATENT DOCUMENTS

| 5,306,299 | A | * | 4/1994 | Applebaum ................. 623/10 |
| 5,514,177 | A | | 5/1996 | Kurz et al. |
| 6,183,255 | B1 | * | 2/2001 | Oshida ..................... 433/201.1 |
| 6,251,138 | B1 | * | 6/2001 | Nadol, Jr. et al. ............ 623/10 |
| 6,712,754 | B2 | * | 3/2004 | Miller et al. .................. 600/25 |
| 6,726,719 | B2 | | 4/2004 | Antonelli et al. |
| 7,087,081 | B2 | | 8/2006 | Prescott et al. |

FOREIGN PATENT DOCUMENTS

WO   WO 03/071992 A2 * 9/2003

* cited by examiner

Primary Examiner—Corrine McDermott
Assistant Examiner—David A. Izquierdo
(74) Attorney, Agent, or Firm—Wood, Phillips, Katz, Clark & Mortimer

(57) ABSTRACT

A titanium incudo-stapedial joint prosthesis comprises a body including a generally tubular wall defining a first cavity for receiving a head of a stapes. A generally U-shaped wall is connected to the tubular wall defining a second cavity extending generally perpendicular to the first cavity for receiving an incus. The tubular wall comprises slots to enable the first cavity to be sized to fit the head of the stapes. The general U-shaped wall comprises slots to enable the second cavity to be sized to fit to the incus.

14 Claims, 2 Drawing Sheets

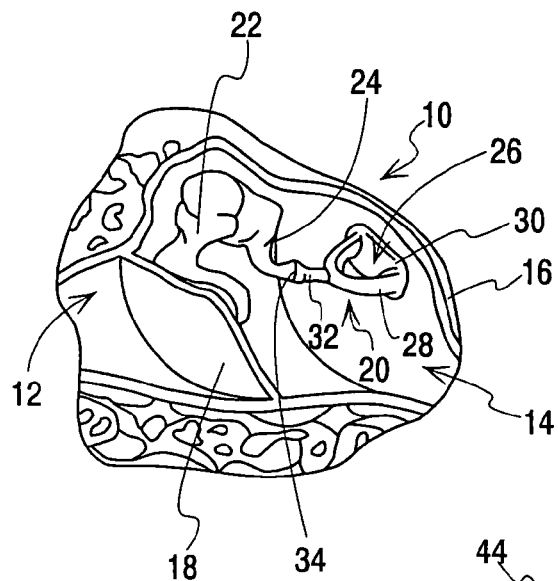
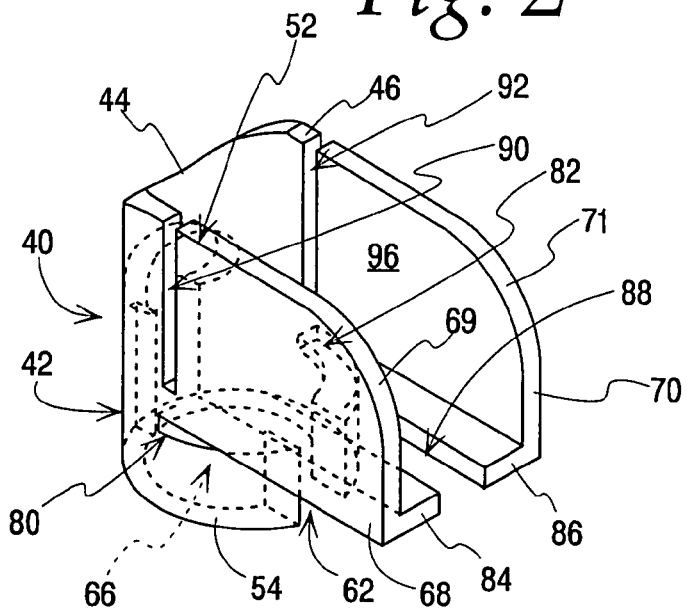
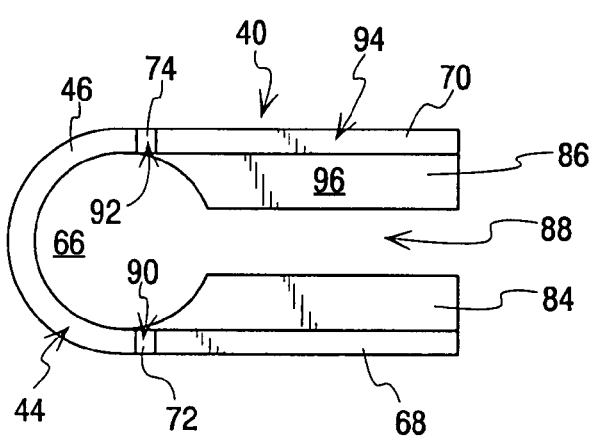
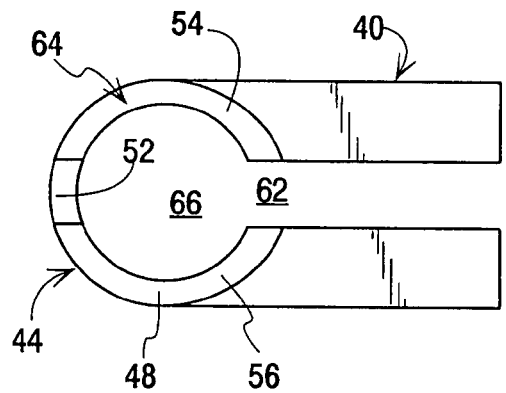

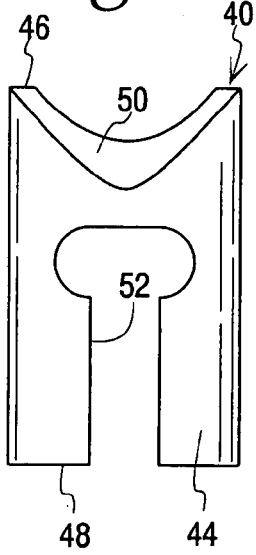
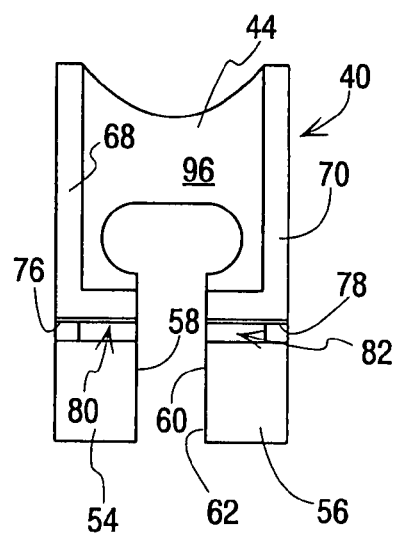
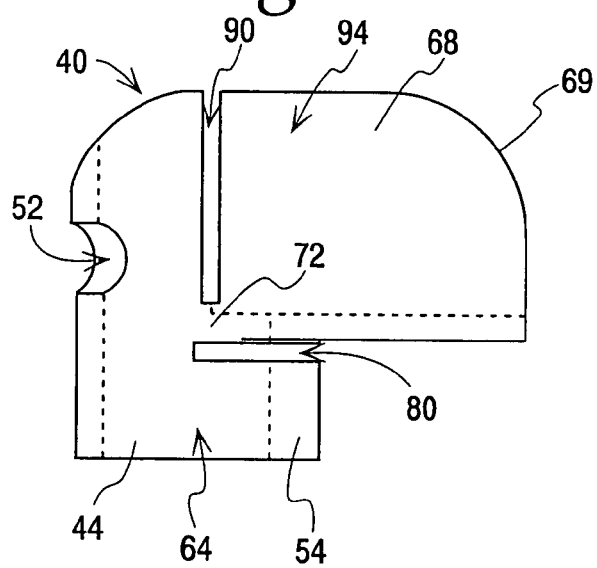
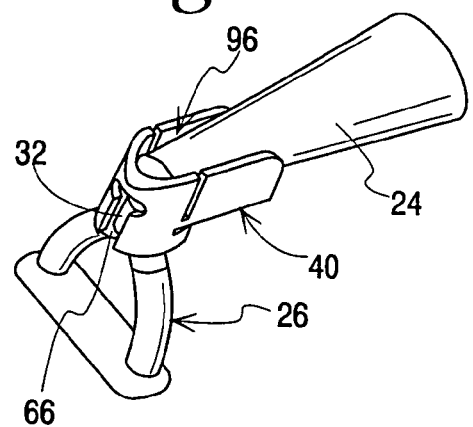

TITANIUM INCUDO-STAPEDIAL JOINT PROSTHESIS

FIELD OF THE INVENTION

This invention relates to an ossicular prosthesis used for replacement and reconstruction and, more particularly, to a titanium incudo-stapedial joint prosthesis.

BACKGROUND OF THE INVENTION

Due to disease, trauma, or congenital malformation, the ossicles of the middle ear are sometimes damaged. The delicate joint between the incus and the stapes is termed the incudo-stapedial joint (ISJ). The ISJ is a cartilaginous joint having a tendency to ossify in older humans. When the joint is interrupted due to erosion of the joint or the incus itself, vibrations can no longer be transmitted from the incus to the stapes. The result is a conductive hearing loss related to the disrupted ossicular chain.

Medical implants have been developed to reconstruct the ossicular chain when a portion of the incus is missing. However, the entire incus had to be removed and replaced with a prosthesis. This approach destroys the natural joint between the incus and stapes and the lever function of the incus in relationship to the malleus and stapes.

One particular implant to address conditions when only the ISJ is eroded or ossified is shown in U.S. Pat. No. 5,306,299. This prosthesis is made from a hydroxylapatite. Particularly, the prosthesis comprises a block of hydroxylapatite having a cylindrical cavity intersecting with a U-shaped channel. The prosthesis is not adjustable. As such, the prosthesis must be provided in different sizes for different size ossicular chains. The prosthesis cannot be adjusted to conform to varying sized incus and stapes. Because of its mass and lack of features to stabilize its connection to the incus and stapes, it is possible for the prosthesis to migrate and extrude through the ear drum over a period of time. Concerns over the weight of the ceramic material and the overall mass of the prosthesis have been raised. Also, the hydroxylapatite material is inherently fragile, prone to breakage and cannot be easily modified to custom fit the incus or stapes head.

The present invention is directed to an adjustable, titanium ISJ prosthesis.

SUMMARY OF THE INVENTION

In accordance with the invention, there is provided an adjustable middle ear prosthesis.

Broadly, there is disclosed in accordance with one aspect of the invention, an adjustable middle ear prosthesis comprising a body of deformable metal capable of retaining different shapes. The body comprises a generally tubular cavity for receiving a head of a stapes and an elongate cavity extending generally perpendicular to the generally tubular cavity for receiving an incus. The body can be reshaped to fit to bones of the stapes and the incus.

It is a feature of the invention that the body comprises a collar defining the generally tubular cavity. The collar has a longitudinally extending through slot.

It is another feature of the invention that the body comprises a collar defining the generally tubular cavity. The collar has a pair of opposite longitudinally extending through slots.

It is another feature of the invention that the body comprises a generally semi-cylindrical wall connected to opposite parallel walls having inwardly extending flanges defining the elongate cavity. The opposite parallel walls are connected to the semi-cylindrical wall by bridges to define elongate slots between the opposite parallel walls and the semi-cylindrical wall. The flanges are spaced apart to define a cavity slot. The body comprises a collar spaced below the opposite parallel walls defining the generally tubular cavity. The collar has a longitudinally extending slot.

It is another feature of the invention that the body is of titanium.

There is disclosed in accordance with another aspect of the invention an adjustable incudo-stapedial joint prosthesis comprising a malleable metal body comprising a generally tubular slotted wall defining a first cavity for receiving a head of a stapes. A generally U-shaped wall is connected to the tubular slotted wall defining a second cavity extending generally perpendicular to the first cavity for receiving an incus. The body can be reshaped to fit bones of the stapes and the incus.

It is a feature of the invention that the body comprises a generally semi-cylindrical wall connected to opposite parallel walls to define a generally U-shaped wall and connected to arcuate wall portions longitudinally spaced from the opposite parallel wall to define a generally tubular slotted wall.

It is another feature of the invention that the generally semi-cylindrical wall includes a keyhole slot.

It is still another feature of the invention that the bodies are of a relatively soft unalloyed titanium.

There is disclosed in accordance with another aspect of the invention a titanium incudo-stapedial joint prosthesis comprising a body comprising a generally tubular wall defining a first cavity for receiving a head of a stapes. A generally U-shaped wall is connected to the tubular wall defining a second cavity extending generally perpendicular to the first cavity for receiving an incus. The tubular wall comprises slots to enable the first cavity to be sized to fit the head of the stapes. The general U-shaped wall comprises slots to enable the second cavity to be sized to fit to the incus.

Further features and advantages of the invention will be readily apparent from the specification and from the drawings.

BRIEF DESCRIPTION OF THE DRAWINGS

FIG. 1 is a perspective, partial cross-section of the anatomy of an ear showing a normal ossicular chain;

FIG. 2 is a perspective view of an adjustable incudo-stapedial joint (ISJ) prosthesis in accordance with the invention;

FIG. 3 is a top plan view of the ISJ prosthesis of FIG. 2;

FIG. 4 is a bottom plan view of the ISJ prosthesis of FIG. 2;

FIG. 5 is a front elevation view of the ISJ prosthesis of FIG. 2;

FIG. 6 is a rear elevation view of the ISJ prosthesis of FIG. 2;

FIG. 7 is a side elevation view of the ISJ prosthesis of FIG. 2; and

FIG. 8 is a perspective view illustrating the ISJ prosthesis in accordance with the invention implanted in a human ear.

DETAILED DESCRIPTION OF THE INVENTION

Referring initially to FIG. 1, a human ear 10 includes an external or outer ear 12, a middle ear 14 and an inner ear 16. A tympanic membrane 18, also called the ear drum, separates the outer ear 12 from the middle ear 14. The middle ear 14 includes an ossicular chain 20 comprising three small bones that are connected and transmit the sound waves from the ear drum 18 to the inner ear 16. The three small bones are called the malleus 22, the incus 24, and the stapes 26. The stapes 26 includes a loop or arch 28 connected to a footplate 30. A head 32 at the top of the arch 28 connects to the incus 24 at an incudo-stapedial joint (ISJ) 34.

In accordance with the invention, an ISJ prosthesis 40, see FIGS. 2–7, is used when only the ISJ is eroded or ossified. As described more particularly below, the ISJ prosthesis 40 is made from a malleable metal, such as titanium. Thus, the weight of the prosthesis is greatly reduced when compared to previous design ISJ prostheses. The mass of the prosthesis 40 is also reduced compared to prior such prostheses and the rounded geometry allows reconnection of the ISJ without introducing sharp edge interference for surrounding structures and bone. Additionally, the ISJ prosthesis 40 contains a series of slots enabling the prosthesis to be adjusted in multiple planes to provide a custom fit to either the incus 24 or the stapes head 32.

The ISJ prosthesis 40 is manufactured of a one piece deformable, malleable metal body 42. For ease of description herein, the body 42 is described referring to the leftmost part in FIGS. 3 and 4 as the front and the right-most part in FIGS. 3 and 4 as the rear. It should be understood, however, that these relative terms are for reference only in describing the device and do not describe any particular characteristics of the prosthesis 40.

The body 42 comprises a generally semi-cylindrical wall 44 having a top end 46 and a bottom end 48. A rounded notch 50 is provided proximate the top end 46. A keyhole slot 52 is provided through the semi-cylindrical wall 44 originating at the bottom end 48.

The semi-cylindrical wall 44 is connected to opposite arcuate wall portions 54 and 56 at its bottom end 48. The arcuate wall portions 54 and 56 have respective distal edges 58 and 60 spaced apart to define a collar slot 62. The semi-cylindrical wall bottom end 48 and the arcuate wall portions 54 and 56 form a bottom tubular wall 64 slotted with the keyhole slot 52 and the collar slot 62. The slotted tubular wall 64 defines a generally tubular cavity 66. The tubular cavity 66 is adapted for receiving the head 32 of the stapes 26 during implantation.

Opposite parallel walls 68 and 70 extend tangentially from the semi-cylindrical wall 44 and are connected thereto by respective bridges 72 and 74. Top rear corners 69 and 71 are rounded. The walls 68 and 70 have respective lower edges 76 and 78 spaced above the respective arcuate wall portions 54 and 56 to define spacer slots 80 and 82. The opposite parallel walls 68 and 70 have inwardly extending, spaced apart flanges 84 and 86 to define an elongate slot 88 therebetween. The opposite parallel walls 68 and 70 are spaced from the semi-cylindrical wall 44 above the respective bridges 72 and 74 to define respective front slots 90 and 92.

The semi-cylindrical wall 44 at the top end 46 and the side walls 68 and 70 form a generally U-shaped wall 94 defining an elongate cavity 96 for receiving an incus 24. As is apparent, the elongate cavity 96 is open from the top or rear for receiving an incus 24 with the incus 24 resting on the flanges 84 and 86. As is apparent, the orientation of the elongate cavity 96 is generally perpendicular to the tubular cavity 66 owing to the conventional relationship in orientation between the incus 24 and stapes head 32.

In accordance with the invention, the body 42 is of one piece construction of a deformable or crimpable metal capable of retaining different shapes. In an exemplary embodiment of the invention, the ISJ prosthesis 40 is formed of an unalloyed titanium for surgical implant applications. For example, the prosthesis 40 may be made of a titanium that satisfies the specifications of AFTM standard F67. This standard identifies four grades of unalloyed titanium for surgical implant applications. The grades are numbered 1, 2, 3 and 4. The grades range from 1 which is a relatively soft titanium that is readily malleable to grade 4 which is relatively hard and more spring-like. Advantageously, the prosthesis 40 is made of a grade 2 titanium to be malleable. As is apparent, it could be made of other grades, most particularly grades 1 or 3 according to an amount of malleability desired.

In an exemplary embodiment to the invention, the prosthesis 40 has a front to rear dimension of about 2.5 mm and a height of about 2.0 mm, and a width of about 1.27 mm. The tubular cavity 66 may have a radius on the order of 0.5 mm. The elongate cavity 96 may have a height of about 1.27 mm, width of about 1.0 mm and length, not including the space above the tubular cavity 66 of about 1.5 mm. The wall thickness is generally uniform and may be on the order of 0.1 mm. The prosthesis 40 may be formed by machining or the like. As is apparent, the dimensions of the prosthesis 40 could be different from that described herein according to the needs within the medical community.

In accordance with the invention, the prosthesis 40 is fabricated of a metal such as titanium and is of a relatively light weight compared to ceramic materials used previously. The prosthesis 40 has a generally tubular shape and is less likely to be displaced because it can be adjusted and/or crimped to the adjoined bones. Particularly, the elongate cavity 96 is adjustable for receiving a portion of the incus 24, as shown in FIG. 8. The elongate cavity 96 is adjustable owing to the malleability of the titanium. Also, the top slots 90, 92 and the elongate slot 88 allow the elongate cavity 96 to be adjusted to fit different diameters of the incus 24. Particularly, the side walls 68 and 70 can be deformed above the flanges 84 and 86 owing to use of the front slots 90, 92. Likewise, the side walls 68 and 70 can be moved closer together by collapsing the sides of the elongate slot 88. The spacer slots 80 and 82, the collar slot 62 and the keyhole slot 52 allow the tubular cavity 66 to be adjusted to fit the head 32 of the stapes 26.

As described, the size and shapes of the cavities 66 and 96 can be adjusted prior to placement on the stapes 26 and incus 24, as shown in FIG. 8. Additionally, the prosthesis 40 can be crimped to the bones of the incus 24 and stapes 26 using a forceps to tighten the connection. As such, the prosthesis 40 does not rely on compression between the malleus 22, the incus 24 and stapes 26 to hold the prosthesis in place until soft tissue encapsulation help stabilize the prosthesis to adjoining bones. Nevertheless, growth of bone tissue will further stabilize the prosthesis 40 as the surface of the titanium body 42 provides a scaffold for on growth.

Thus, in accordance with the invention, there is provided an adjustable ISJ prosthesis.

We claim:

1. An adjustable middle ear prosthesis comprising:
   a body of deformable metal capable of retaining different shapes, the body comprising a generally tubular cavity for receiving the head of a stapes and an elongate cavity extending generally perpendicular to the generally tubular cavity for receiving an incus, a generally semi-cylindrical wall to define a generally U-shaped wall and connected to opposite parallel walls having inwardly extending flanges defining the elongate cavity, and a collar spaced below the opposite parallel wall defining the generally tubular cavity, the collar having a longitudinally extending through slot, wherein the body can be reshaped to fit to bones of the stapes and the incus.

2. The adjustable middle ear prosthesis of claim 1 wherein the collar has a pair of opposite longitudinally extending through slots.

3. The adjustable middle ear prosthesis of claim 1 wherein the opposite parallel walls are connected to the semi-cylindrical wall by bridges to define elongate slots between the opposite parallel walls and the semi-cylindrical wall.

4. The adjustable middle ear prosthesis of claim 1 wherein the flanges are spaced apart to define a cavity slot.

5. The adjustable middle ear prosthesis of claim 1 wherein the body is of titanium.

6. An adjustable incudo-stapedial joint prosthesis comprising:
a malleable metal body comprising a generally tubular slotted wall defining a first cavity for receiving a head of a stapes and a generally U-shaped wall connected to the tubular slotted wall defining a second cavity extending generally perpendicular to the first cavity for receiving an incus, wherein the body comprises a generally semi-cylindrical wall connected to opposite parallel walls to define the generally U-shaped wall and connected to arcuate wall portions longitudinally spaced from the opposite parallel walls to define the generally tubular slotted wall, wherein the body can be reshaped to fit to bones of the stapes and the incus.

7. The adjustable incudo-stapedial joint prosthesis of claim 6 wherein the opposite parallel walls have inwardly extending, spaced apart flanges for supporting the incus.

8. The adjustable incudo-stapedial joint prosthesis of claim 6 wherein the opposite parallel walls are connected to the generally semi-cylindrical wall by bridges to define elongate slots between the opposite parallel walls and the semi-cylindrical wall.

9. The adjustable incudo-stapedial joint prosthesis of claim 6 wherein the generally semi-cylindrical wall includes a keyhole slot.

10. The adjustable incudo-stapedial joint prosthesis of claim 6 wherein the body is of titanium.

11. The adjustable incudo-stapedial joint prosthesis of claim 6 wherein the body is of a relatively soft unalloyed titanium.

12. A titanium incudo-stapedial joint prosthesis comprising:
a body comprising a generally tubular wall defining a first cavity for receiving a head of a stapes and a generally U-shaped wall connected to the tubular wall defining a second cavity extending generally perpendicular to the first cavity for receiving an incus, the tubular wall comprising slots to enable the first cavity to be sized to fit the head of the stapes and the generally U-shaped wall comprising slots to enable the second cavity to be sized to fit the incus, the body further comprising a generally semi-cylindrical wall connected to opposite parallel walls to define the generally U-shaped wall and connected to arcuate wall portions longitudinally spaced from the opposite parallel walls by spacer slots to define the generally tubular wall, wherein the opposite parallel walls are connected to the generally semi-cylindrical wall by bridges to define elongate slots between the opposite parallel walls and the semi-cylindrical wall.

13. A titanium incudo-stapedial joint prosthesis comprising:
a body comprising a generally tubular wall defining a first cavity for receiving a head of a stapes and a generally U-shaped wall connected to the tubular wall defining a second cavity extending generally perpendicular to the first cavity for receiving an incus, the tubular wall comprising slots to enable the first cavity to be sized to fit the head of the stapes and the generally U-shaped wall comprising slots to enable the second cavity to be sized to fit the incus, the body further comprising a generally semi-cylindrical wall connected to opposite parallel walls to define the generally U-shaped wall and connected to arcuate wall portions longitudinally spaced from the opposite parallel walls by spacer slots to define the generally tubular wall, wherein the generally semi-cylindrical wall includes a keyhole slot and distal edges of the arcuate wall portions are spaced apart to define a collar slot.

14. A titanium incudo-stapedial joint prosthesis comprising:
a body comprising a generally tubular wall defining a first cavity for receiving a head of a stapes and a generally U-shaped wall connected to the tubular wall defining a second cavity extending generally perpendicular to the first cavity for receiving an incus, the tubular wall comprising slots to enable the first cavity to be sized to fit the head of the stapes and the generally U-shaped wall comprising slots to enable the second cavity to be sized to fit the incus, the body further comprising a generally semi-cylindrical wall connected to opposite parallel walls to define the generally U-shaped wall and connected to arcuate wall portions longitudinally spaced from the opposite parallel walls by spacer slots to define the generally tubular wall wherein the opposite parallel walls have inwardly extending flanges for supporting the incus, the flanges being spaced apart to define a cavity slot.

* * * * *